United States Patent [19]

Krall et al.

[11] 4,045,486

[45] Aug. 30, 1977

[54] PROCESS FOR PREPARING AZOMETHINES

[75] Inventors: Hermann-Dieter Krall, Meerbusch; Hans-Helmut Schwarz, Krefeld, both of Germany

[73] Assignee: Bayer Aktiengesellschaft, Leverkusen, Germany

[21] Appl. No.: 685,557

[22] Filed: May 12, 1976

[30] Foreign Application Priority Data

June 6, 1975 Germany ............................ 2525295

[51] Int. Cl.² ............................................ C07C 119/00
[52] U.S. Cl. .................................................. 260/566 R
[58] Field of Search .................................... 260/566 R

[56] References Cited

U.S. PATENT DOCUMENTS 3,219,704  11/1965  Wilder et al. ................... 260/566 R

FOREIGN PATENT DOCUMENTS 1,396,762  6/1975  United Kingdom ............ 260/566 R

*Primary Examiner*—Gerald A. Schwartz
*Attorney, Agent, or Firm*—Burgess, Dinklage & Sprung

[57] ABSTRACT

Azomethines having the formula

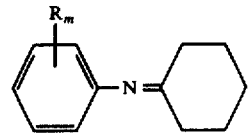

wherein
  R is hydrogen, alkyl or alkoxy,
  $m$ denotes an integer of from 1 to 4, and
  the $m$ radicals are the same or different, are prepared by condensing cyclohexanone and a primary aromatic amine in the presence of an acid ion exchanger.

7 Claims, No Drawings

PROCESS FOR PREPARING AZOMETHINES

BACKGROUND

This invention relates to a process for the preparation of azomethines from cyclohexanone and primary aromatic amines in the presence of acid ion exchangers.

The condensation of cyclohexanone and aniline to N-cyclohexylidene-aniline with zinc chloride-aniline has long been known (Berichte der Deutschen chemischen Gesellschaft, Volume 53 (1920), pages 345 to 354). A process for the preparation of imines, using aromatic amines and aliphatic, cycloaliphatic or aromatic ketones as the starting materials, in which the reaction is carried out by circulating a mixture of the two reagents through a stationary bed of molecular sieves is also known from German Published Application No. 2,244,238; aniline and cyclohexanone are mentioned, inter alia, as starting materials. However, these known processed are subject to disadvantages which are serious for carrying out the processes industrially. In the first case, expensive working up is necessary in order to isolate the reaction product; in the latter case the water absorption capacity of the molecular sieves is restricted by their nature and after a certain time expensive desorption of water and organic material must follow.

In addition, Example 6 of German Published Application No. 1,493,942 describes the preparation of a small amount of N-cyclohexylidene-aniline by heating aniline and cyclohexanone in a molar ratio of 1 : 5 at 100° to 110° C for 1.5 hours, the water which is eliminated being distilled off. This process also cannot be used on an industrial scale, since, according to our own experiments, the rate of reaction decreases when there is a smaller excess of cyclohexanone and the rate of evaporation of the water formed decreases with larger reaction volumes as a result of the longer diffusion path; moreover, because of the larger excess of cyclohexanone, considerable technical effort is necessary for apparatus for the appropriate dimensions and for separating off the excess cyclohexanone by distillation.

SUMMARY

It has now been found that azomethines of the formula

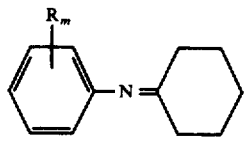

(I)

in which
R represents hydrogen or alkyl or alkoxy radicals and
$m$ denotes an integer of from 1 to 4, and
the $m$ R radicals are the same or different,
are obtained in good yield by condensation of cyclohexanone and primary aromatic amines of the formula

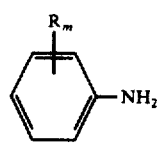

(II)

in which
R and $m$ have the abovementioned meaning,
when the condensation is carried out in the presence of an acid ion exchanger.

DESCRIPTION

Possible alkyl radicals of straight-chain and branched alkyl radicals have up to 4, preferably 1 and 2, carbon atoms. Examples which may be mentioned are: methyl, ethyl, propyl, isopropyl, butyl, isobutyl and tert.-butyl, preferably methyl and ethyl.

The range of meaning for the alkoxy radicals corresponds to the abovementioned range of meaning for the alkyl radicals.

Cyclohexanone is known; a large number of primary aromatic amines of the formula II are also known.

Acid ion exchangers which can be used are both weakly acid and strongly acid ion exchangers.

Examples of weakly acid ion exchangers which may be mentioned are polyacrylates which contain carboxyl groups and are crosslinked with divinylbenzene.

Examples of strongly acid ion exchangers which may be mentioned are styrene/divinylbenzene copolymers containing sulphonic acid groups.

The degree of crosslinking of the polymer and its structure are only of secondary importance; for example, the divinylbenzene content in the polymer can be between 2 and 18 percent by weight.

Likewise, the polymers to be used according to the invention can have a gel-like or a macroporous structure.

A preferred group of weakly acid ion exchangers, which can be used in the process according to the invention, is known from German Published Application No. 1,595,700.

A preferred group of strongly acid ion exchangers, which can be used in the process according to the invention, is known from J. appl. Chem., Volume 1, (1951), pages 124 -132.

They are prepared by bead polymerisation of styrene and divinylbenzene and subsequent sulphonation of the cross-linked polystyrene and have a gel-like structure.

Amongst the macroporous ion exchangers, a group which can preferably be used in the process according to the invention is known from German Published Specification No. 1,113,570. The macroporous structure for these styrene/divinylbenzene copolymers is obtained by adding, to the suspension of the monomers in water, an organic solvent which, during the subsequent polymerisation, leads to the sponge structure of the resins. The polymer obtained is then sulphonated in the customary manner.

In general, the ion exchangers which can be used according to the invention are employed in the acid form, in which they are usually obtained from their preparation; a large number of these ion exchangers are commercially available and are then supplied in the acid form.

However, it is also possible to use ion exchangers which are partially in the neutral form, the proton in the acid group of the exchangers being replaced in a known manner by a cation, preferably an alkali metal or alkaline earth metal cation, for example of sodium, potassium, magnesium or barium.

In general, ion exchangers are obtained from their preparation in a water-containing form; it is then appropriate to remove the adhering water and/or the absorbed water in a known manner before they are used according to the invention. For this purpose it can be particularly advantageous to employ the known azeotropic distillation with organic solvents, cyclohexanone appropriately being employed as the entraining agent.

Using aniline as an example, the process according to the invention is illustrated by the equation which follows:

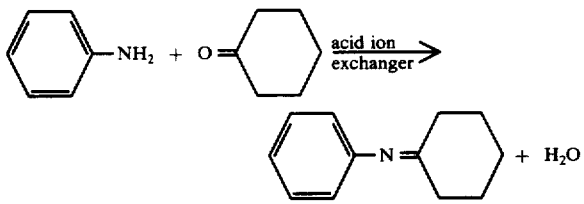

In general, the process according to the invention is carried out in a temperature range between 60° and 120° C, preferably between 80° and 115° C and especially between 100° and 110° C.

Although the process according to the invention can also be carried out under normal pressure or elevated pressure, in which case, however, side reactions may be favoured, it is preferably carried out under reduced. Appropriately, the pressure is between 300 and 100 mbars, preferably between 250 and 150 mbars and especially between 230 and 170 mbars.

In general, the process according to the invention is carried out by adding the ion exchanger to be used to the reaction mixture of cyclohexanone and the primary amine of the formula II and heating the reaction mixture to the chosen reaction temperature, preferably to the boil, the pressure being selected accordingly, and removing the water of reaction which is formed during the condensation.

This can be effected, for example, by using an organic solvent, which optionally has a lower boiling point than cyclohexanone, such as benzene or toluene, as the entraining agent for the azetropic distillation of the water of reaction.

Advantageously, however, the procedure employed for distilling off the water of reaction is that an excess of cyclohexanone is used and the water formed is distilled off with this azeotropically and, after pass separation in the distillate and after separating off the water, the cyclohexanone is recycled continuously or batchwise into the reaction mixture.

Since, in the process according to the invention, cyclohexanone can serve both as a reactant in the reaction according to the invention and also, advantageously, as an entraining agent for the water which is formed during the reaction, when this is removed by azeotropic distillation, it is preferably used in excess of the stoichiometrically required amount of 1 mol per mol of aromatic amine of the formula II.

In general, 1.5 to about 10 mole of cyclohexanone, preferably 1.8 to 5.0, and especially about 2 to 3, mols of cyclohexanone per mol of amine are used.

The course of the reaction can be followed easily by known analytical methods for example by measuring the amount of water which has passed over or by measuring the water content and the amount of the distillate which passes over.

When the reaction is complete, the reaction product can be isolated in a known manner, for example by filtering off the ion exchanger and distilling off the excess cyclohexanone; if appropriate, the azomethine obtained can be purified in a known manner, for example by fractional distillation.

The process according to the invention can be carried out both batchwise and continuously. The apparatus can be designed in a known manner, corresponding to the state of the art.

Azomethines of the formula I are not only highly useful as intermediates in preparing secondary amines such as unsubstituted or substituted dicyclohexylamines, N-cyclohexylanilines or diphenylamines, but are useful per se as antioxidants for various substances such as gasoline and as accelerators in the vulcanization of rubber.

The advantage of the process according to the invention lies, in particular, in the shorter reaction times, the higher conversion per unit time and the smaller reactor volumes which are necessary, that is to say the higher conversion per unit volume required, compared with the state of the art.

The practicability of the process according to the invention is surprising since it is known from German Patent Specification No. 857,960 that cyclohexanone condenses in the presence of cation exchangers based on synthetic resins, at elevated temperature, to give cyclohexenyl-cyclohexanone.

EXAMPLES

The term "relative degree of conversion C" used in the Examples which follow is calculated according to the following definition:

$$C = [1 - \frac{\text{amount of amine still present}}{\text{initial amount of amine}}] \times 100 \, [\%].$$

The apparatus used in the Examples which follow consisted of a 6,000 ml stirred flask fitted with a water separator and a reflux condenser so that only the organic phase from the distillate flowing back passed into the reaction vessel. The apparatus was connected to a vacuum pump via a control unit, so that it was possible to set up a reduced pressure at any desired level in the apparatus.

The ion exchangers used in the Examples which follow were obtained as follows:

The gel-like ion exchangers A, B and C were prepared according to J. appl. Chem., Volume 1 (1951), page 131. A shaking vessel of correspondingly greater capacity was used in place of the beer bottle; the amounts of styrene and divinylbenzene solution which were used as indicated below; the amounts of benzoyl peroxide and the aqueous solution of the emulsifier were adjusted accordingly.

| Exchanger | ml of styrene | ml of divinylbenzene (approximately 50% strength solution, remainder ethyl styrene) |
|---|---|---|
| A | 960 | 40 |
| B | 920 | 80 |
| C | 840 | 160 |

The macroporous ion exchangers D, E and F were prepared according to German Published Specification No. 1,113,570, Example 3. The amounts of styrene, technical grade divinylbenzene (approximately 50% strength solution, remainder ethylstyrene) and white spirit (boiling point 140° to 190° C) which are indicated below were used in each case; the amounts of benzoyl peroxide and water, which contained 0.1% of methylcellulose in solution, were adjusted accordingly.

| Exchanger | g of styrene | g of divinylbenzene | g of white spirit |
| --- | --- | --- | --- |
| D | 420 | 80 | 300 |
| E | 380 | 120 | 250 |
| F | 320 | 180 | 325 |

The weakly acid ion exchanger G was prepared according to German Published Application No. 1,595,700, Example 9. by copolymerisation of acrylonitrile with 8% of divinylbenzene and subsequent alkaline hydrolysis.

Table I which follows summarises the properties of the exchangers obtained.

Table I

| Exchanger | Degree of crosslinking (%) | Grain size (mm) | Water content (%) | Capacity (moist) (milliequivalent/ml) |
| --- | --- | --- | --- | --- |
| A | 2 | 0.3 – 1.2 | 70 | 0.8 |
| B | 4 | 0.3 – 1.2 | 65 | 1.3 |
| C | 8 | 0.3 – 1.2 | 45 | 2.1 |
| D | 8 | 0.3 – 1.2 | 45 | 1.4 |
| E | 12 | 0.3 – 1.2 | 50 | 1.8 |
| F | 18 | 0.3 – 1.2 | 55 | 1.6 |
| G | 8 | 0.3 – 1.0 | 50 | 4.5 |
| H | 8 | 0.3 – 1.0 | 70 | 0.2 |

EXAMPLE 1 (Preparation of the anhydrous ion exchangers)

In each case 1,302 g (14 mols) of aniline and 2,744 g (28 mols) of cyclohexanone as well as 607 g of the ion exchangers the properties of which are indicated in Table I are heated, whilst stirring and under reflux, in the apparatus described above, until the separation of water has ceased. During this time care is taken by appropriate regulation of the pressure in the apparatus to ensure that the sump temperature does not exceed 120° C and that the mixture boils continuously.

When the separation of water is complete, the mixture is cooled and the ion exchanger is filtered off, washed several times with a total of 500 ml of cyclohexanone and suction-drained thoroughly. The anhydrous ion exchanger, which is thus obtained in the cyclohexanone-moist state, is used in Example 2 to 8 which follow.

EXAMPLES 2 to 8

In each case 1,302 g of aniline and 2,744 g of cyclohexanone were heated, whilst stirring, in the apparatus described above, with, in each case, 200 g of the cyclohexanonemoist ion exchanger described in Table I and obtained according to Example 1, the pressure in the apparatus being so regulated that the reaction mixture boiled continuously but its temperature did not exceed 110° C. The ion exchanger was then filtered off and the filtrate was distilled in vacuo, excess cyclohexanone being separated off.

Table II which follows gives the Example No., the nature of the ion exchanger used, according to the description in Table I, the maximum temperature of the reaction mixture, the pressure range during the reaction, the reaction time and the relative degree of conversion C.

EXAMPLE 9 (Comparison Example)

1,302 g of aniline and 2,744 g of cyclohexanone were reacted in the manner described for Examples 2 to 8 without the addition of an iron exchanger. The result obtained is also indicated in Table II.

EXAMPLE 10

1,200 ml of the exchanger A, described above, were suspended in 3,000 ml of water and 115 ml of 20% strength by weight aqueous sodium hydroxide solution were added, whilst stirring. The exchanger was then filtered off and rinsed with water.

15 ml of the exchanger A which has gas thus been partially converted into the neutral form, and which is designated exchanger H, were suspended in 100 ml of distilled water; after adding 20 g of solid sodium chloride, the suspension was stirred for one hour and then titrated with 0.5 N NaOH, using bromocresol blue as the indicator, in order to determine the capacity. The properties of exchanger H are also given in Table I.

Exchanger H was dehydrated as described above in Example 1 and then used for the condensation of aniline and cyclohexanone, as described in Examples 2 to 8.

The reaction conditions and the results obtained are also given in Table II.

Table II

| Example | Ion Exchanger | Maximum temperature (° C) | Pressure range (mbars) | Reaction time (minutes) | C % |
| --- | --- | --- | --- | --- | --- |
| 2 | A | 108 | 226 – 146 | 345 | 100 |
| 3 | B | 109 | 226 – 173 | 215 | 100 |
| 4 | C | 105 | 226 – 173 | 300 | 100 |
| 5 | D | 107 | 226 – 187 | 270 | 100 |
| 6 | E | 109 | 226 – 160 | 270 | 100 |
| 7 | F | 108 | 226 – 173 | 375 | 100 |
| 8 | G | 108 | 226 – 173 | 265 | 100 |
| 9 | — | 108 | 226 – 200 | 540 | 87 |
| 10 | H | 109 | 226 – 173 | 180 | 100 | low.

EXAMPLES 11 to 14

The procedure described in Examples 5 and 9 was followed, only 1,302 g of aniline were replaced by 1,498 g of o-toluidine or 1,694 g of o-phenetidine. The reaction time was restricted to 3 hours in both experiments. After this time, the relative degree of conversion was determined from the analytical results. Table III which follows gives the maximum reaction temperature during the reaction and the relative degree of conversion. The results show that conversion is considerably more rapid when, according to the invention, an ion exchanger is used.

Table III

| Example | Amine | Ion Exchanger | Maximum temperature (° C) | Pressure range (mbars) | C (%) |
|---|---|---|---|---|---|
| 11* | o-Toluidine | — | 110 | 200 – 146 | 40 |
| 12 | " | D | 110 | 200 – 113 | 80 |
| 13* | o-Phenetidine | — | 105 | 200 – 160 | 22.2 |
| 14 | " | D | 110 | 200 – 133 | 53.4 |

*Comparison Examples

EXAMPLES 15 to 20 (Comparison Examples)

Cyclohexanone and aniline were reacted in a molar ratio of 5 : 1, without the use of a catalyst, in reactors of different volumes, the water of reaction, which distils off azeotropically with cyclohexanone, being removed and the cyclohexanone being recycled after separating off the water which, on cooling, separates out as a second phase. Table IV which follows gives the amount of cyclohexanone and aniline, the maximum reaction temperature, the pressure range during the reaction, the reaction time and the relative degree of conversion C determined after this time.

The Examples show that the reaction without a catalyst, according to German Published Application No. 1,493,942, cannot be used on an industrial scale.

Table IV

| Example No. | Cyclohexanone (g) | Aniline (g) | Reactor volumes (l) | Reaction time (hours) | Relative degree of conversion C (%) |
|---|---|---|---|---|---|
| 15 | 150 | 28 | 0.5 | 2 | 96 |
| 16 | 600 | 112 | 1.0 | 2 | 96 |
| 17 | 2,400 | 448 | 4.0 | 7 | 83 |
| 18 | 3,600 | 672 | 6.0 | 8.5 | 85 |
| 19 | 23,400 | 4,400 | 40.0 | 20 | 76 |
| 20 | 140,500 | 26,500 | 200.0 | 21 | 63 |

What is claimed is:

1. Process for preparing an azomethine of the formula

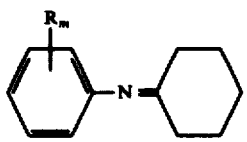

wherein $R$ is hydrogen, alkyl or alkoxy, $m$ denotes an integer of from 1 to 4, and the $m$ R radicals are the same or different, which comprises condensing cyclohexanone and a primary aromatic amine of the formula

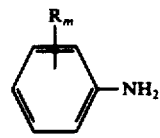

wherein $R$ and $m$ are as defined above.

in the presence of an acid ion exchanger.

2. Process of claim 1 wherein the reaction is carried out at a temperature of from 60° to 120° C.

3. Process of claim 1 wherein the reaction is carried out under reduced pressure.

4. Process of claim 1 wherein the reaction is carried out at a pressure of from 100 and 300 mbars.

5. Process of claim 1 wherein from 1.5 to 10 mols cyclohexanone are used per mol of primary aromatic amine.

6. Process of claim 1 wherein the acid ion exchanger is a polyacrylate containing carboxyl groups and crosslinked with divinylbenzene.

7. Process of claim 1 wherein the acid ion exchanger is a styrene/divinylbenzene copolymer.

* * * * *